United States Patent [19]
Plumley

[11] Patent Number: 5,891,125
[45] Date of Patent: Apr. 6, 1999

[54] DISPOSABLE ABSORBENT ARTICLE WITH SELF ADAPTING BODY FACING SURFACE TOPOGRAPHY

[75] Inventor: Julian Ashton Plumley, Warsaw, Poland

[73] Assignee: The Procter & Gamble Company, Cincinnati, Ohio

[21] Appl. No.: 793,221

[22] PCT Filed: Aug. 15, 1995

[86] PCT No.: PCT/US95/10354

§ 371 Date: Apr. 3, 1997

§ 102(e) Date: Apr. 3, 1997

[87] PCT Pub. No.: WO96/05791

PCT Pub. Date: Feb. 29, 1996

[30] Foreign Application Priority Data

Aug. 24, 1994 [EP] European Pat. Off. ............ 94202428.2

[51] Int. Cl.[6] ...................................................... A61F 13/15

[52] U.S. Cl. ......................................... 604/385.1; 604/387
[58] Field of Search ............................. 604/385.1, 385.2, 604/387, 369

[56] References Cited

U.S. PATENT DOCUMENTS

| | | | |
|---|---|---|---|
| 5,330,459 | 7/1994 | Lavon et al. | 604/385.1 |
| 5,505,720 | 4/1996 | Walters et al. | 604/385.1 |
| 5,520,674 | 5/1996 | Lavon et al. | 604/385.2 |

*Primary Examiner*—Robert A. Clarke
*Attorney, Agent, or Firm*—Edward J. Milbrada; Jeffrey V. Bamber; Steven W. Miller

[57] ABSTRACT

The present invention relates to disposable absorbent articles comprising a gas bubble (6) to raise the body facing surface (2) of the article towards the wearer especially in the area of liquid discharge. The gas bubble (6) is filled with gas such that it yields to external pressures in order to maintain a comfortable fit of the absorbent article.

10 Claims, 1 Drawing Sheet

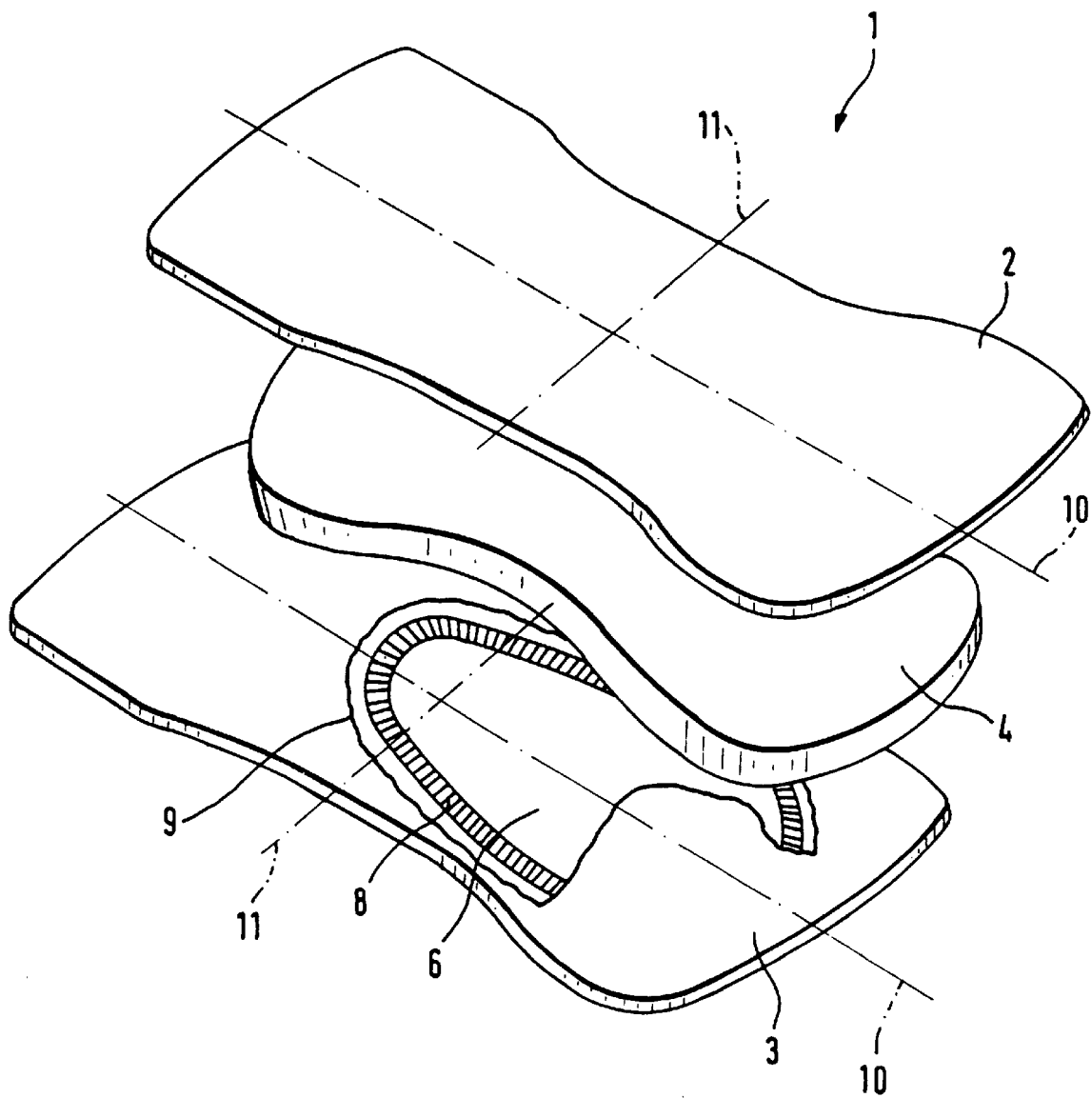

DISPOSABLE ABSORBENT ARTICLE WITH SELF ADAPTING BODY FACING SURFACE TOPOGRAPHY

This is a 371 of PCT/US95/10354 which is the PCT filing of European application 94202428.2 filed on Aug. 24, 1994.

FIELD OF THE INVENTION

The present invention relates to disposable absorbent articles comprising a gas bubble to raise the body facing surface of the article towards the wearer especially in the area of liquid discharge. In particular the present invention relates to sanitary napkins, catamenials incontinence inserts and pantyliners comprising an air bubble between backsheet and absorbent core to raise the absorbent core and the topsheet towards the perineal area of female users. The gas bubble is filled with gas such that it yields to external pressures in order to maintain a comfortable fit of the absorbent article.

BACKGROUND OF THE INVENTION

The basic problem of achieving an absorbent article which closely contacts the body surface around the liquid discharge area of wearers of such articles has been addressed by various designs heretoforth. However, the designs and features suggested in this respect can be further improved for comfort and convenience in respect to the widely varying surface topography of different wearers. This is underlined by the lack of widely available products having features which raise the body facing surface towards the wearer.

WO-9207535 discloses topsheet raising devices in the form of resilient longitudinal spacing structures. The spacing structure is activated by side pressure from the thighs of the wearer. WO-9014063 discloses a hose-like absorption body which also spaces the topsheet away from the absorbent core thereby producing a void space for additional absorption capacity in an absorbent product. U.S. Pat. No. 4,846,824 discloses a labia-pad which is anatomically conformed by folding and confining the product into a raised shape. None of these three prior art disclosures refers to hermetically enclosed gas bubbles to provide the desired shaping function.

GB-1,462,467 discloses an absorbent pad construction designed for heavy-load bearing bed pads. GB-1,575,363 discloses bed pads or sanitary dressings having a backsheet of particular resiliency. U.S. Pat. No. 4,723,953 also discloses a particularly soft bed pad construction showing good resiliency. These three documents all refer to a bubble pack type of construction of the impermeable backsheet in order to provide resiliency for the whole of the absorbent article. No particular area in the topsheet is raised to register with any part of the human body according to these disclosures. U.S. Pat. No. 3,881,491 and U.S. Pat. No. 3,921,232 both relate to activatable gas bubbles designed to provide resiliency and form the absorbent article surface into such a shape that it provides for particular benefits in acquiring bodily exudates. Both documents particularly relate to the separation of feces by providing pockets within the body-facing surface of the absorbent article. These designs have the drawback that they need an activation liquid usually urine. On top of that, the uncertainty in gas amount created raises questions of consistency of design and function.

It is therefore an objective of the present invention to provide an absorbent article with a gas bubble which is yielding so as to comfortably conform the body-facing surface of the article to the individual topography of the wearer particularly in the area of liquid discharge.

BRIEF DESCRIPTION OF THE INVENTION

According to the present invention a disposable article for absorbing liquid by placing it adjacent a body discharge area is provided. The article has a body-facing surface, typically provided by a liquid permeable substrate of fibrous or film-like structure; a garment facing surface, typically provided by a liquid impermeable substrate and an absorbent core placed between the body facing surface and the garment facing surface. The absorbent article has a longitudinal and a lateral axis and is characterised by comprising a yielding gas bubble, preferably an air bubble, to raise the body facing surface towards the liquid discharge area of the wearer.

The shape and size of the bubble may vary considerably from round to rectangular and elliptical shapes or even combinations thereof. Also the gas bubble can be oriented asymmetrically in the absorbent article, typically in relation to the lateral axis.

The gas bubble is preferably placed between the absorbent core and the garment facing surface in order to raise the body facing surface without obstructing the liquid passage to the core while raising the core to also follow the body facing surface topography. The gas bubble is contained in an essentially gas impermeable material like polyethylene, polypropylene, polyethylen terephtalat, aluminium or mixtures or laminates of these materials.

DESCRIPTION OF THE DRAWING

FIG. 1 shows an exploded view of a preferred embodiment of a sanitary napkin according to the present invention comprising an air bubble integrally formed on the backsheet below the absorbent core.

DETAILED DESCRIPTION OF THE INVENTION

The disposable article for absorbent liquid is described below by reference to a sanitary napkin or catamenial. However products such as baby diapers, adult incontinence inserts, or pantyliners may similarly be supplied with the characterising feature of the present invention. A preferred embodiment of a sanitary napkin according to the present invention is shown in a exploded view in FIG. 1. A liquid permeable topsheet (2) overlays an absorbent core (4) which overlays a liquid impermeable backsheet (3). An air bubble (6) is formed by joining the material forming the skin of the air bubble along an endless line (8) to the backsheet (3). The endless line (8) is close to the perimeter (9) of the skin forming material of the air bubble (6) but not necessarily coinciding with the perimeter (9).

Gas bubble

The gas bubble can comprise essentially any gas desired but preferably air. The bubble can be formed from any material which provides a sustainable internal amount of air over the expected product lifetime from manufacturing of the absorbent product to the disposal thereof.

The material used for the bubble should be soft and compliant in order to allow the deformation of the bubble. Typical materials can be those also used for impervious backsheets as well as polyethylene terephtalat and aluminium or mixtures and laminates of these materials.

The bubble may be formed separately or as an integral part of the backsheet as shown in FIG. 1. If formed separate from the backsheet it is desired to immobilise the bubble in relation to the product such that it cannot dislocate during manufacturing, transport, storage and use of the absorbent product. This may be achieved in any usual way but typically would by means of an adhesive. If the gas bubble is formed as an integral part of the backsheet the backsheet must also be impermeable to the gas with which the bubble is filled.

The bubble may be placed between the topsheet (2) and the absorbent core (4) but could then obstruct the liquid passage from the liquid permeable topsheet to the absorbent core. Therefore it preferably is placed between the absorbent core (4) and the backsheet (3).

The gas bubble is typically longer along the longitudinal axis (10) than wide along the lateral axis (11). Also the bubble may have a variety of shapes which are typically symmetrical to the longitudinal axis (10) but asymmetrical to the lateral axis (11). The function of the bubble may also be provided by a number of smaller individual bubbles which in combination provide the desired shape. In particular 2 or 3 bubbles to allow a gradient of the amount of raising the body facing surface and folding lines between the bubbles can replace a single bubble.

If the gas bubble is formed integral with the backsheet as shown in FIG. 1 the joining along line 8 needs to be gas impermeable. This joining may be achieved by such methods as welding, ultrasonic bonding or adhesive attachment.

The bubble is typically filled such that the filling volume is substantially below its maximum filling volume in order to provide a wobbly, flexible and easily deformable outer surface. This ability to deform, also referred to as yielding, provides the desired exceptional ability to adapt the surface topography of the bubble and the overlying absorbent core and topsheet to the topography of the individual wearer of an absorbent product according to the present invention. By filling the bubble no more than 90%, preferably no more than 80% of the maximum volume of the bubble it is possible to ensure that even under the temperature changes common during the wearing of such a product the air bubble will continue to be yielding such that it adapts the product to the wearer's topography.

As an alternative the material forming the skin of the gas bubble at least on its body facing side may be elastic in order to provide the gas bubble with the desired/yielding characteristic. The filling of the bubble in this case can exceed 100% or even 150% of the unstretched bubble volume.

Topsheet

The topsheet (2) is compliant, soft feeling, and non-irritating to the wearer's skin. The topsheet also can have elastic characteristics allowing it to be stretched in one or two directions. Further, the topsheet is fluid previous permitting fluids (e.g., menses and/or urine) to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present invention are selected from high loft nonwoven topsheets and aperture formed film topsheets. Apertured formed films are especially preferred for the topsheet because they are previous to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Particularly preferred microapetured formed film topsheets are disclosed in U.S. Pat. No. 4,609,518 and U.S. Pat. No. 4,629,643. The preferred topsheet for the present invention is the formed film described in one or more of the above patents and marketed on sanitary napkins by The Procter & Gamble Company of Cincinnati, Ohio as "DRI-WEAVE."

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer through the topsheet faster than if the body surface was not hydrophilic. In a preferred embodiment, surfactant is incorporated into the polymeric materials of the formed film topsheet such as is described in U.S. Statutory Invention Registration No. H1670, published on Jul. 1, 1997, in Aziz, et al. Alternatively, the body surface of the topsheet can be made hydrophilic by treating it with a surfactant such as is described in U.S. Pat. No. 4,950,254.

Absorbent Core

The absorbent core is shown as a single entity (4) in FIG. 1. It can include the following components: (a) optionally a primary fluid distribution layer preferably together with a secondary fluid distribution layer; (b) a fluid storage layer; (c) optionally a fibrous ("dusting") layer underlying the storage layer; and (d) other optional components.

The gas bubble typically is placed between the core and the backsheet or the topsheet. However for cores constructed of more than one layer the gas bubble can also be placed between the layers of the core. Also the gas bubble may reach into the core by having the respective space provided in a particular layer. Generally, but in particular if layered core structures of the laminate type are employed, the core should allow the bubble to provide it's yielding function. This can be ensured by rendering the core extensible at least in the region adjacent the gas bubble.

a. Primary Secondary Fluid Distribution Layer

One optional component of the absorbent cores according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized.

b. Fluid Storage Layer

Positioned in fluid communication with, and typically underlying the primary or secondary distribution layers, is a fluid storage layer. The fluid storage layer can comprise any usual absorbent material or combinations thereof. It preferable comprising absorbent gelling materials usually referred to as "hydrogels," "superabsorbent" "hydrocolloid" materials.

These absorbent gelling materials are capable of absorbing large quantities of aqueous body fluids, and are further capable of retaining such absorbed fluids under moderate pressures. These absorbent gelling materials can be in the form of discrete particles. The absorbent gelling materials can be dispersed homogeneously or non-homogeneously in a suitable carrier.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 reissued as RE 32,649. Preferred monomers include acrylic acid, methacrylic acid, and 2-acrylamido-2-methyl propane sulfonic acid. Acrylic acid itself is especially preferred for preparation of the polymeric gelling material.

Suitable carriers include materials which are conventionally utilized in absorbent cores such as cellulose fibers, in the form of fluff. Modified cellulose fibers such as the stiffened cellulose fibers can also be used. Synthetic fibers can also be used and include those made of cellulose acetate,- polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., that lower rewet problems.

If dispersed non-homogeneously in a carrier, the storage layer can be locally homogeneous, i.e. have a distribution gradient in one or several directions within the dimensions of the storage layer. Nonhomogeneous distribution can also refer to laminates of carriers enclosing absorbent gelling materials partially or fully.

c. Optional Fibrous ("Dusting") Layer

An optional component for inclusion in the absorbent cores according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macrostructures such as fibers, sheets or strips, this fibrous "dusting" layer need not be included. However, this "dusting" layer provides some additional fluid-handling capabilities such as rapid wicking of fluid along the length of the pad.

d. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention.

Another component which can be included in the absorbent core according to the invention and preferably is provided close to or as part of the primary or secondary fluid distribution layer are odor control agents. Typically active carbon coated with or in addition to other odor control agents, in particular suitable zeolite or clay materials, are optionally incorporated in the absorbent core. These components can be incorporated in any desired form but often are included as discrete particles.

Backsheet

The backsheet (3) prevents the exudates absorbed and contained in the absorbent core from wetting articles that contact the absorbent product such as underpants, pants, pajamas and undergarments. The backsheet (3) is preferably impervious to liquids (e.g., menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Indiana, under the designation XP-39385. The backsheet is preferably embossed and/or matte finished to provide a more clothlike appearance. Further, the backsheet can permit vapors to escape from the absorbent structure (i.e., be breathable) while still preventing exudates from passing through the backsheet.

If the backsheet forms part of the skin of the gas bubble according to the present invention it needs to be impermeable at least in the area of the gas bubble.

Optional Components of the Absorbent Products

Optionally, the absorbent product of the present invention can comprise all those components typical for the particularly intended product use. For example catamenials, panty liners and sanitary napkins often comprise components such as wings and panty fastening adhesives in order to improve their positioning and soiling protection performance. Leg elastication by one or several elastic strands is also common in the art of absorbent products. In general, all typically used components in absorbent products can also be comprised in the absorbent products according to the present invention as long as a gas bubble is present.

What is claimed is:

1. A disposable absorbent article for wearing adjacent a body discharge area, said article having a body facing surface, a garment facing surface and an absorbent core between said body facing surface and said garment facing surface and further having a longitudinal axis and a lateral axis, said article comprising a yielding gas bubble wherein said gas is at a pressure greater than the surrounding atmospheric pressure so as to raise said body facing surface towards said discharge area.

2. A disposable absorbent article according to claim 1 wherein said gas bubble is an air bubble.

3. A disposable absorbent article according to claim 1 wherein said gas bubble is oriented asymmetrically to said lateral axis.

4. A disposable absorbent article according to claim 1 wherein said gas bubble is enclosed in a film, the material of said film being selected from the group consisting of polyethylene, polypropylene, polyethyleneterephthalat, aluminum, mixtures thereof or laminates thereof.

5. A disposable absorbent article according to claim 1 wherein said gas bubble is longer along said longitudinal axis than along said lateral axis.

6. A disposable absorbent article according to claim 1 wherein said gas bubble has a shape selected from the group consisting of rectangular shapes, round shapes, elliptical shapes or combinations thereof.

7. A disposable absorbent article according to claim 1 wherein said body facing surface is provided by a liquid permeable substrate and said garment facing surface is provided by a liquid impermeable substrate.

8. A disposable absorbent article according to claim 1 wherein said gas bubble is placed between said garment facing surface and said absorbent core.

9. A disposable absorbent article according to claim 8 wherein said garment facing surface is provided by a liquid and gas impermeable film which film also forms part of said gas bubble.

10. A disposable absorbent article according to claim 1 wherein said disposable absorbent article is a sanitary napkin or a panty liner.

* * * * *

UNITED STATES PATENT AND TRADEMARK OFFICE
CERTIFICATE OF CORRECTION

PATENT NO.   : 5,891,125
DATED        : April 6, 1999
INVENTOR(S)  : Julian Ashton Plumley It is certified that error appears in the above-identified patent and that said Letters Patent is hereby corrected as shown below:

Column 1,
Line 60, between "liquid" and "usually" please insert -- , -- (a comma).

Column 3,
Lines 51 and 67, please delete "previous" and insert therefor -- pervious --.

Column 4,
Line 28, between "in" and "Aziz" please insert -- the name of --.
Line 51, between "Primary" and "Secondary" please insert -- / -- (a slash).

Column 5,
Line 33, after "acetate," please delete "-" (the hyphen).
Line 46, please delete "Nonhomogeneous" and
insert therefor -- Non-homogeneous --.

Signed and Sealed this

Eleventh Day of February, 2003

JAMES E. ROGAN
*Director of the United States Patent and Trademark Office*